Figure 1:
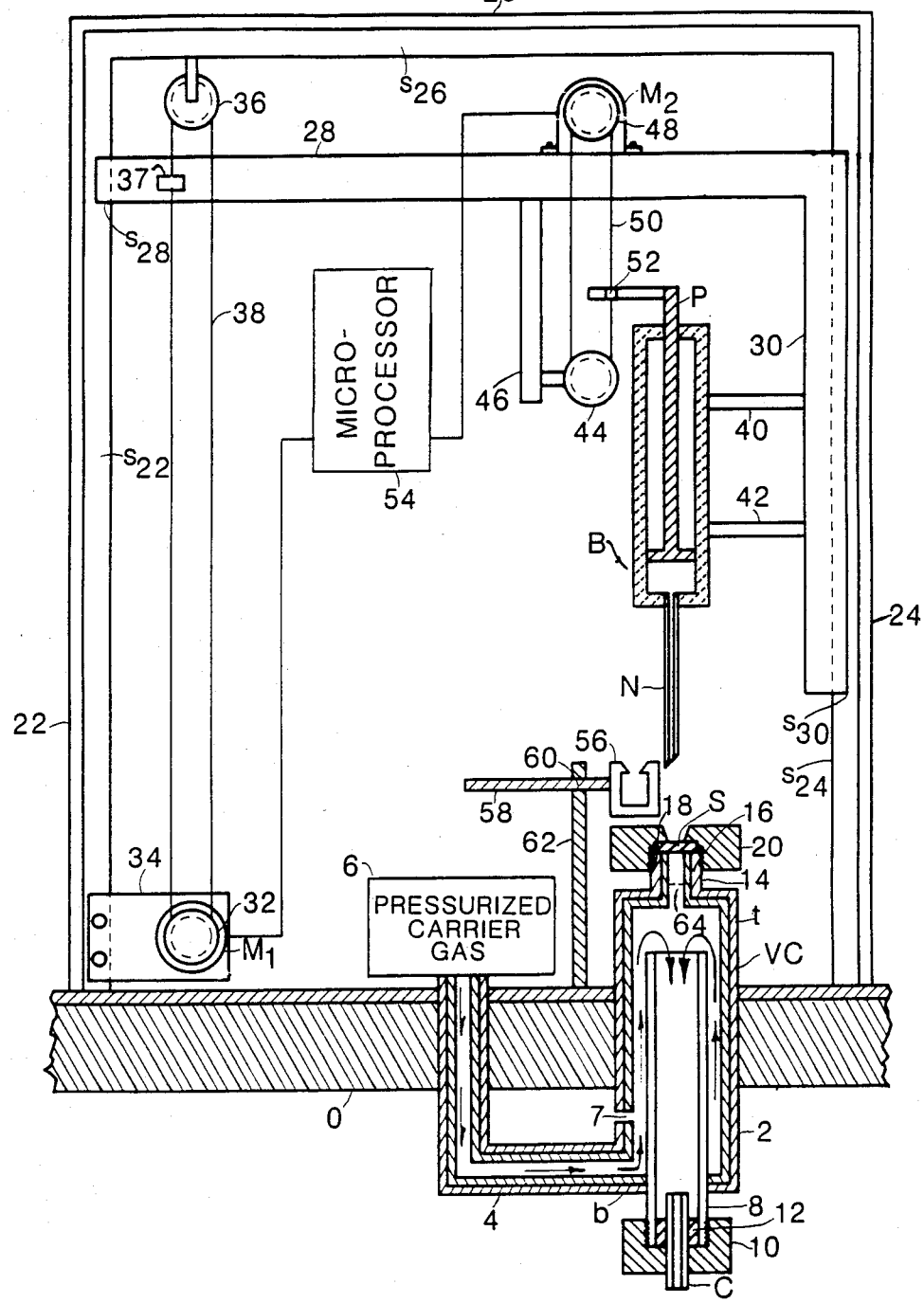

United States Patent [19]

DiNuzzo et al.

[11] Patent Number: 4,615,226

[45] Date of Patent: Oct. 7, 1986

[54] APPARATUS AND METHOD FOR INTRODUCING SOLUTES INTO A STREAM OF CARRIER GAS OF A CHROMATOGRAPH

[75] Inventors: Francis M. DiNuzzo, Landenberg, Pa.; James S. Fullemann, Half Moon Bay, Calif.

[73] Assignee: Hewlett-Packard Company, Palo Alto, Calif.

[21] Appl. No.: 697,659

[22] Filed: Feb. 4, 1985

[51] Int. Cl.$^4$ .................. G01N 1/00; G01N 1/14; G01N 1/28

[52] U.S. Cl. .................. 73/864.87; 73/863.11; 73/864.86; 73/864.24; 73/864.16

[58] Field of Search .......... 73/864.81, 864.85, 864.86, 73/864.87, 864.16, 864.21, 864.24, 864.74, 863.11, 863.12, 23.1, 61.1 C, 864.25, 864.82, 864.83, 864.84; 436/181; 422/78, 80

[56] References Cited

U.S. PATENT DOCUMENTS

| | | | |
|---|---|---|---|
| 3,327,535 | 6/1967 | Sequeira | 73/864.24 X |
| 3,374,660 | 3/1968 | McKinney et al. | 73/23.1 |
| 3,401,565 | 9/1968 | Stoll et al. | 73/863.11 |
| 3,482,450 | 12/1969 | Harris, Sr. et al. | 73/864.86 |
| 3,501,176 | 3/1970 | Arms | 73/864.86 X |
| 3,581,573 | 6/1971 | Purcell et al. | 73/863.11 |
| 3,733,909 | 5/1973 | Golovistikov | 73/864.86 |
| 3,748,911 | 7/1973 | Rousselet et al. | 73/864.25 X |
| 3,985,016 | 10/1976 | Horuki | 73/864.86 |
| 4,038,874 | 8/1977 | Baldin et al. | 73/864.87 X |
| 4,166,094 | 8/1979 | Froehlich et al. | 73/864.25 |
| 4,414,857 | 11/1983 | Brazhnikov et al. | 73/864.87 X |

FOREIGN PATENT DOCUMENTS

| | | | |
|---|---|---|---|
| 23959 | 7/1972 | Japan | 73/864.86 |
| 156862 | 12/1980 | Japan | 73/864.86 |

OTHER PUBLICATIONS

"Dipping Chromatograph Tube Collects Microgram Samples"; *Control Engineering;* vol. 8, No. 10, p. 121; Oct. 1961; R. C. Palmer.

"Glass Copillary GC with On-Column Injection"; *Laboratory Equipment Digest;* vol. 17, No. 6, pp. 71, 73 & 75; Jun. 1979; Charles D. Cook.

"The Influence of the Syringe Needle on the Precision and Accuracy of Vaporizing GC Injections"; *Journal of High Resolution Chromatography & Chromatography Communications;* Jan. 1979; pp. 15-21; K. Grob, Jr. et al.

"Evaluation of Syringe Handling Techniques for Injections into Vaporizing GC Injectors"; *Journal of HRC & CC,* vol. 3, Dec. 1980; K. Grob, Jr. et al.; pp. 627-633.

*Primary Examiner*—Stewart J. Levy
*Assistant Examiner*—Tom Noland
*Attorney, Agent, or Firm*—Donald N. Timbie

[57] ABSTRACT

A precise volume of sample liquid is injected by inserting a syringe into the vaporizing chamber of the injection assembly for a gas chromatograph by performing the entire injection including withdrawal of the syringe in such a short time that essentially none of the liquid is vaporized while in the needle.

5 Claims, 4 Drawing Figures

APPARATUS AND METHOD FOR INTRODUCING SOLUTES INTO A STREAM OF CARRIER GAS OF A CHROMATOGRAPH

BACKGROUND OF THE INVENTION

The amounts of different solutes contained in a solvent can generally be determined by a gas chromatograph if the solutes are vaporizable at temperatures not in excess of 400° C. A gas chromatograph is comprised of means for providing a stream of carrier gas, means for introducing solutes from a sample of the solute containing solvent into the stream an oven, a separation column within the oven that elutes the solutes contained in the stream at respectively different times, and a detector for indicating the respective amounts of those solutes as they elute.

An early and widely used means for introducing a sample of solvent into a stream of carrier gas includes a syringe and a heated vaporization chamber through which the stream is made to flow. The temperature of the vaporization chamber is set above the vaporization temperature of the least volatile solute of interest, and a desired volume of sample liquid is injected into the needle of the syringe by operation of the plunger so as to force at least some of the liquid into the vaporization chamber. Non-volatile components in the sample are left in the needle or are deposited on the walls of the vaporization chamber and do not enter the column.

A number of techniques have been developed for operating the syringe, but all of them exhibit discrimination against the less volatile solutes of a sample, i.e., as the volatility decreases below a given value, the amount introduced into the stream decreases. This has led to the suggestion that the needle be left in the vaporization chamber for several seconds so that the solvent and all the solutes in the needle are vaporized, but this does not reduce the discrimination to a level at which it can be ignored. Furthermore, the amount of solutes that reaches the stream of carrier gas varies from injection to injection. Various tedious calibration techniques can be used to compensate for these phenomena. Another difficulty with these injection methods of the prior art is that the vaporization of components in the needle makes it difficult to input sample volumes that are a small fraction of the volume of the needle.

In order to obtain accurate results without employing time-consuming calibration techniques, it is essential that the solutes from a predetermined volume of sample and only that volume be introduced into the stream of carrier gas. This can be done by employing a "cold on-column injection technique" wherein the top of a "T" coupling is inserted in the separating column through which low temperature carrier gas is flowing to the separation column and the sample volume of solvent containing the solutes of interest is injected via the needle of a syringe into the carrier gas through the stem of the T. Unfortunately, however, insoluble components may be present in the sample, resulting in damage to the column. In some cases, the column must be discarded and in others, a piece must be broken off and the remaining portion recalibrated. In addition, this technique is only applicable to very dilute samples and it requires a time-consuming cooling of the oven between injections.

These matters are discussed in an article by K. Grob Jr. and H. P. Neukom, entitled "The Influence of the Syringe Needle on the Precision and Accuracy of Vaporizing GC Injections" which was published during January 1979 in the *Journal of HPC and CC* at page 15 and in an article by K. Grob and S. Rennhard, entitled "Evaluation of Syringe Handling Techniques for Injection into Vaporizing GC Injectors" which was published during December 1980 in the same journal at page 627.

BRIEF SUMMARY OF THE INVENTION

In accordance with this invention, the steps of inserting the syringe needle into the vaporization chamber, operating the plunger of the syringe and withdrawing the needle from the vaporization chamber are all done in such a short time that the needle does not get hot enough to vaporize a significant amount of the solvent or of any solute. Thus, a sample volume leaves the needle as a liquid, the vaporizable components thereof assume gaseous form in the vaporization chamber so as to enter the stream of carrier gas, the non-vaporizable components remain in the needle or the chamber, no components are vaporized from the solvent solution that pushes the sample volume out of the needle, and there is little or no discrimination.

It has been found that the performance described above can be attained for solvents such as hexane that boil at 69° C. by making the total time that the top of the needle dwells in the vaporization chamber 500 milliseconds or less. For solvents that boil at lower temperatures, the dwell time should be reduced. Satisfactory operation is attained when pentane is used as a solvent if the dwell time is 76 milliseconds.

A significant advantage of this invention is the fact that the solutes that only come from sample volumes that are a fraction of the needle volume may be introduced into the stream of carrier gas. This is possible because the purely hydraulic injection of the sample volume into the vaporization chamber can be precisely controlled and nothing is added by vaporization as in the prior art.

BRIEF DESCRIPTION OF THE DRAWINGS

FIG. 1 is a partial cross-section illustrating apparatus for performing the insertion and withdrawal of the needle as required;

FIG. 2 is a timing diagram for the insertion and withdrawal of the needle as well as for the injection;

FIG. 3 contains a series of graphs that respectively indicate the discrimination resulting from different injection techniques; and FIG. 4 is a graphical comparison of "on column" injection and injection in accordance with this invention insofar as discrimination is concerned.

DETAILED DESCRIPTION OF THE INVENTION

In FIG. 1, which illustrates one embodiment of the invention, O indicates a portion of the top of the oven of a gas chromatograph and VC indicates a vaporization chamber extending therethrough. The vaporization chamber VC includes a hollow cylinder 2 that is coupled via a tube 4 to a source 6 of pressurized carrier gas and a tube 8 that is coaxially mounted within the cylinder 2 and extends through the bottom b thereof. If sample splitting is desired, an opening 7 is provided in the cylinder 2 near the bottom b. The bottom of the tube 8 is coupled via a nut 10 and packing 12 to a separating column C that extends into the tube 8. A short section of another tube 14 is coaxially mounted to the top t of the cylinder 2 so as to communicate therewith. The top of the tube 14 has an inner recess 16 in which a septum S of perforable rubber-like material is mounted. The septum S extends above the upper end of the tube 14 and into a recess 18 in a nut 20 having inner threads engaging threads on the outside of the tube 14. A stream of carrier gas flows through the tube 4 into the cylinder 2, up to the top of the tube 8, and downwardly in the tube 8 to the column C as indicated by the arrows.

A U-shaped bracket comprised of vertical side members 22 and 24 and a horizontal top member 26 is attached to the top portion O of the oven so that the horizontal member 26 is spaced therefrom. Although not shown, all of these members have a T-shaped cross-section and are oriented with their respective stems $s_{22}$, $s_{24}$ and $s_{26}$ facing inwardly. A carriage comprised of a horizontal arm 28 and a vertical arm 30 is slidably mounted on the vertical side members 22 and 24. In this particular illustration, the end of the horizontal arm 28 has a slot $s_{28}$ therein that fits snugly over the stem $s_{22}$ of the vertical member 22; and the vertical arm 30 has a slot $s_{30}$ along its outer edge that fits snugly over the stem $s_{24}$ of the of the vertical member 24. Thus, the stems $s_{22}$ and $s_{24}$ of the vertical members 22 and 24 form rails or guides along which the carriage 28, 30 can travel in a vertical direction.

The amount and direction of travel is controlled in the following manner. A stepping motor $M_1$ having a pulley 32 mounted to one end of its shaft is attached by a bracket 34 to the vertical member 22, and a pulley 36 is suspended from the horizontal member 26. A belt 38 that is entrained over the pulleys 32 and 36 is clamped to the horizontal arm 28 of the carriage at 38 so as to cause it to be moved up or down depending on the direction of rotation of the stepping motor $M_1$.

A hollow cylindrical barrel portion B of a syringe having a reservoir therein and a hollow needle N extending axially downward therefrom is mounted by brackets 40 and 42 to the vertical arm 30 of the carriage 28, 30. A plunger P is mounted in the barrel portion B of the syringe with a slide fit that is tight enought to permit it to move easily and yet draw liquid into the needle N and the barrel B when it is moved upward. A pulley 44 is mounted for rotation on an axle that is affixed to a bracket 46 extending downwardly from the horizontal arm 28 of carriage 28, 30 and a DC motor $M_2$ that is mounted on the horizontal arm 28 drives a pulley 48. A belt 50 is entrained over the pulleys 44 and 48 and is clamped to the top of the plunger P at 52 so that the plunger is moved up or down depending on the direction of rotation of the motor $M_2$. The motors $M_1$ and $M_2$ may be controlled in any suitable manner or by a microprocessor 54.

The solution to be analyzed may be located in a cup 56 that is mounted on the end of a bar 58 that can be slid in either direction as required by hand or by connecting it to an automatic or semi-automatic translation device (not shown) of well known type by obvious techniques within a horizontal hole 60 in a vertical bar 62 that is secured to the top O of the oven. In more sophisticated equipment, a number of sample cups could be carried at circumferentially displaced points on a tray that is rotated in a horizontal plane about a vertical axis so as to bring the cups in line with the needle N. A U-shaped opening is provided in the outer edge of the tray that can be rotationally positioned so as to permit the barrel B to pass through it when an injection is to be made. If desired, the rotation of the tray can also be controlled by the microprocessor 54.

In operation, a sample is first loaded into the barrel B of the syringe. The cup 56 is positioned under the needle N and the barrel portion B is lowered by the stepping motor $M_1$ until the tip of the needle N is immersed in the solution. The motor $M_2$ then operates to raise the plunger P so as to draw solution into the barrel B. The amount in the barrel B depends on the volume of the sample to be injected and can than be less or greater than the volume of the needle N. When this is done, the motor $M_1$ raises the barrel B of the syringe and the cup 56 is moved from under the needle N.

When sample fluid is to be introduced into the stream of carrier gas, the motor $M_1$ rapidly lowers the carriage 28, 30 until the bottom of the barrel B approaches the nut 20 at which point the top of the needle N is at a level indicated by a dashed line 64 in FIG. 1.

Figure 2:
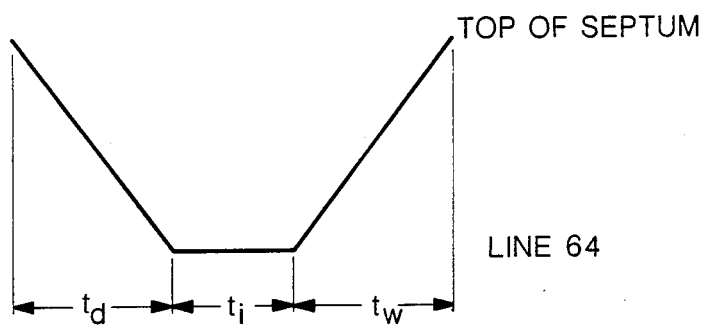

FIG. 2 illustrates the various steps of an injection procedure. During the period $t_d$, the tip of the syringe needle N is moving downward from the septum S. Note that the dashed line 64 is above the top of the tube 8. This is to make it possible for nonvolatile components to strike the inner walls of the vaporization chamber where they will be retained and prevented from reaching the stream of carrier gas denoted by the arrows. The tip of the needle N remains in the lowest position during a period $t_i$ and the motor $M_2$ lowers the plunger P until it has displaced a desired sample volume from the end of the needle N. During a period $t_w$, the motor $M_1$ withdraws the barrel B and the needle N until the tip of the needle N is just above the bottom of the septum S. It would be possible to lower the plunger P during portions of either or both of $t_d$ and $t_w$ in addition to $t_i$. It would also be possible for the motor $M_1$ to immediately start raising the barrel B as soon as it reaches its lowest point. Another variation would be to raise the plunger P as soon as it has expelled the sample volume of liquid. FIG. 2 indicates that the velocity with which the syringe is lowered and raised are the same and constant, but this too can be varied. Whichever of these combinations are used, it is important that there be as little evaporation of solutes from the needle during the entire dwell time of $t_d+t_i+t_w$. Experience has shown that when hexane is used as the solvent, good results are attained if the dwell time $t_d+t_i+t_w$ is 500 milliseconds or less because hexane which is a typical solvent of high volatility, is not vaporized. If more volatile solvents such as pentane are used, it is preferable to reduce the dwell time to a point well below 500 milliseconds.

Figure 3:
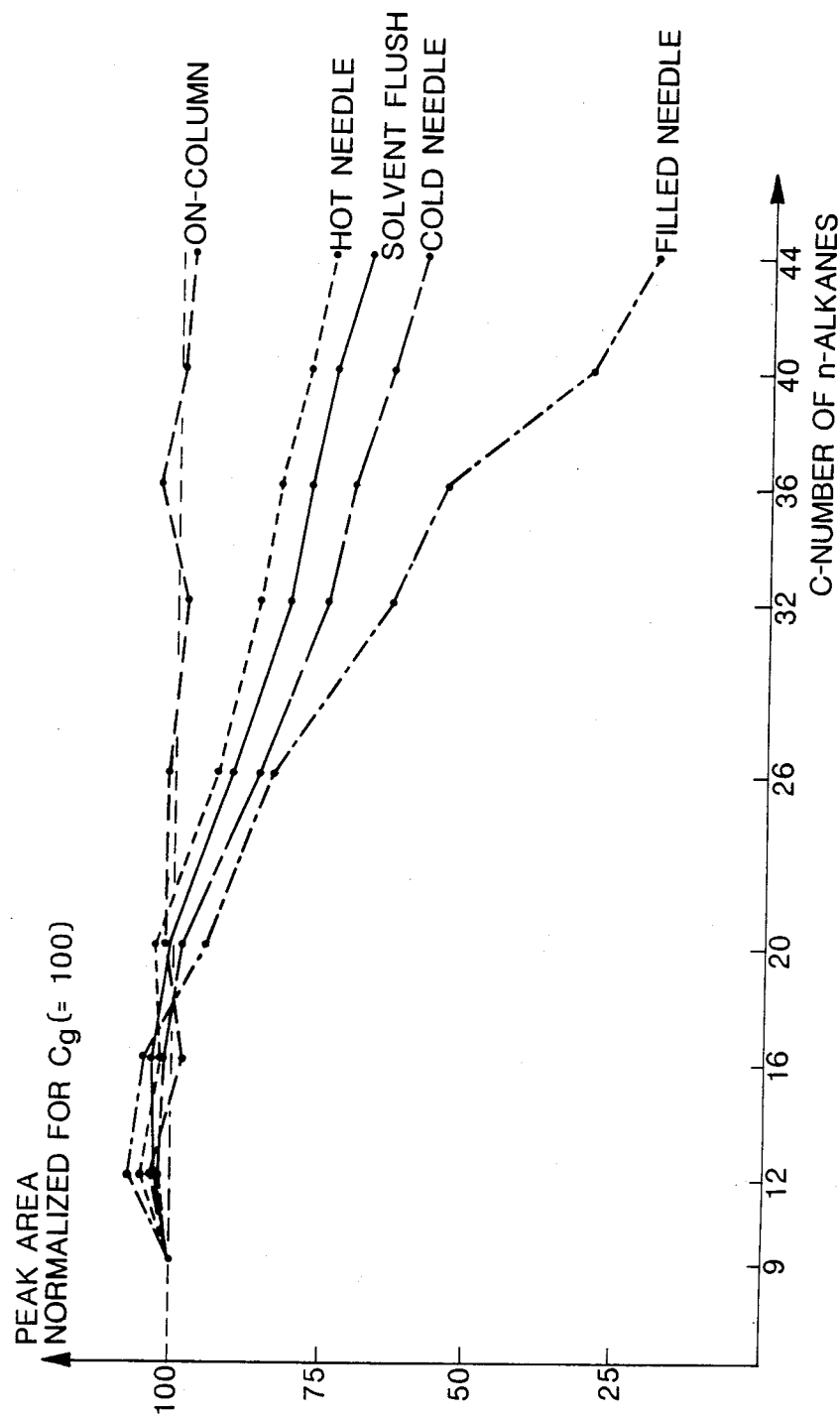

FIG. 3 shows graphically the results attained by several injection methods of the prior art when normalized on the nonane peak with the temperature of the vaporization chamber at 350° C. and a one-microliter sample injected with a 15:1 split. The amount of the alkane having a C-number of 44 that is introduced into the stream of carrier gas in only 25% of the nonane that is introduced when the full needle method of injection, which is the one generally used by automatic injection means, is employed. Whereas the percentage improved to 75% for the best prior art method of injection wherein the solvent is drawn into the barrel and the needle heated in the vaporization chamber prior to injection, this still requires the use of calibration techniques. The fact that these graphs all converge at 100% for nonane and the fact that all the nonane in a sample volume displaced by the plunger of a syringe is introduced into the stream of carrier gas by the "on-column"

method does not mean that the other methods do the same because all of these measurements are relative. When using these other methods, one must use a calibration technique that can compensate for the fact that the solutes actually introduced into the stream of carrier gas can come from a volume of solvent solution that is different and usually greater than the sample volume and which can also compensate for the discrimination.

Figure 4:
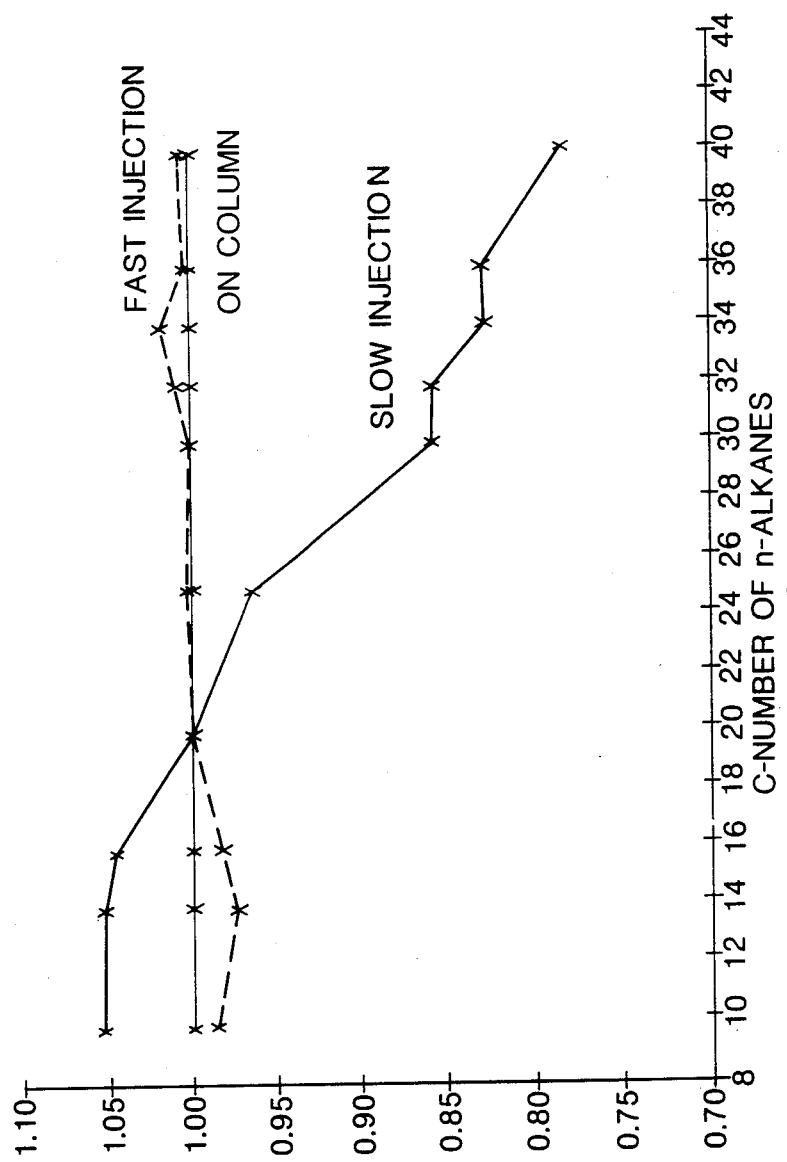

FIG. 4 shows a comparison of the discrimination encountered when using a full needle injection having the usual dwell time with an injection having the short dwell time of this invention as well as the discrimination encountered with on-column injection. The results are normalized on an alkane having a C-number of 20, the sample volume displaced by the plunger is one microliter, the temperature of the vaporization chamber was set to 350° C., and the solvent was hexane. Note that the prior art method having a dwell time of three seconds intoduces relatively more of the alkane having C-numbers less than 20 into the carrier gas stream than it does of C-20, even though the amounts of all alkanes in the test sample were the same.

In these graphs, all alkanes are respectively normalized to the alkanes in the on-column injection so that it is considered to be 100%. The important fact is that the discrimination resulting from using the short dwell time of this invention is within ±3% of that attained by the on-column method so as not to require calibration. Furthermore, the solutes introduced into the stream of carrier gas are all of those in the sample volume and no more, so that compensation for variable volumes is not required.

What is claimed is:

1. A method of injecting sample liquid into a vaporization chamber, comprising the steps of
    drawing sample liquid into a syringe,
    inserting a needle of the syringe into a heated vaporizing chamber for a period that is less than 500 miliseconds, and
    operating the syringe so as to inject a sample volume of liquid into the vaporizing chamber while the needle is inserted therein.

2. Apparatus for injecting sample liquid into a vaporization chamber, comprising
    a syringe having a hollow needle projecting from a reservoir,
    means operable to cause said syringe to draw sample liquid into said needle and said reservoir,
    means operable to cause said syringe to expel liquid from said needle,
    said vaporizing chamber having three openings therein, one of said openings being closed by a septum, a second of said openings being attachable to a separating column, and a third of said openings being attachable to a source of carrier gas under pressure whereby when said latter attachment is made a stream of carrier gas flows through said chamber between said second and third openings,
    means for moving the syringe so as to cause the tip of its needle to pierce said septum and enter said vaporizing chamber and for subsequently withdrawing said needle from said vaporizing chamber within 500 milliseconds, and
    means for causing said syringe to eject liquid through said needle while the tip thereof is inside said vaporizing chamber.

3. A method of introducing a sample volume of a solute containing solvent into a vaporization chamber of an injection means for a gas chromatograph comprising the steps of
    inserting a needle of a syringe into the vaporization chamber,
    operating the syringe before components in the needle are vaporized so as to hydraulically inject a sample volume of solvent into the chamber in liquid form, and
    withdrawing the needle from the vaporization chamber before a significant amount of any component therein is vaporized.

4. A method as described in claim 3 in which the tip of the needle is in the vaporization chamber for no more than 500 milliseconds.

5. A methed of introducing a sample volume of a solute containing solvent into a vaporization chamber of an injection means for a gas chromatograph comprising the steps of
    inserting a needle of a syringe into said vaporization chamber,
    withdrawing the needle from the chamber,
    operating the syringe while the needle is in the vaporization chamber so as to inject a sample volume into the chamber,
    all of the said steps being performed in no more than 500 milliseconds.

* * * * *